United States Patent [19]

Urushizaki et al.

[11] Patent Number: 4,877,730

[45] Date of Patent: Oct. 31, 1989

[54] MICROBIOLOGICAL METHOD FOR PRODUCING ETHYLENE

[75] Inventors: Sueo Urushizaki, Sakura; Yasuo Ohta, Tsu; Mamoru Sato; Sakai: Fukumi, both of Ibaraki; Koushi Nishiyama, Yatabe, all of Japan

[73] Assignee: Director of National Institute of Agrobiological Resources, Ibaraki, Japan

[21] Appl. No.: 891,254

[22] Filed: Jul. 28, 1986

[30] Foreign Application Priority Data

Aug. 23, 1985 [JP] Japan .................................. 60-184299

[51] Int. Cl.⁴ ........................... G12P 5/02; G12P 7/00
[52] U.S. Cl. .................................... 435/132; 435/167; 435/874; 435/253.3
[58] Field of Search ............. 435/132, 167, 874, 253.3

[56] References Cited

PUBLICATIONS

Goto et al., *Plant Cell Physiol.* vol. 26, pp. 141-150, 1985 (Jan.).

*Primary Examiner*—Charles F. Warren
*Assistant Examiner*—Irene Marx
*Attorney, Agent, or Firm*—Frishauf, Holtz, Goodman & Woodward

[57] ABSTRACT

A microbiological method for producing ethylene in which a bacterial species *Pseudomonas syringae* pv. *glycinea* or, in particular, a strain of KN 38, KN 41 or KN 50 of the species is cultured. Preferable conditions for culturing are disclosed. The efficiency of the bacteria for the production of ethylene is so high in comparison with other known ethylene-producing bacteria that a possibility of at least partly replacing conventional sources of ethylene is foreseen.

7 Claims, 1 Drawing Sheet

MICROBIOLOGICAL METHOD FOR PRODUCING ETHYLENE

BACKGROUND OF THE INVENTION

The present invention relates to a method for producing ethylene or, more particularly, to a microbiological method for producing ethylene in a high efficiency.

Needless to say, ethylene is one of the most important base materials in the petrochemical industry and produced and consumed in large quantities, mainly, as a starting material of various kinds of synthetic resins including polyethylene as the most typical one. Ethylene is produced in the chemical industry almost exclusively from petrified underground resources such as natural gas and petroleum while exhaustion of such resources is a very serious issue due to the limited amounts of their underground deposits as estimated.

Accordingly, it is an urgent problem to develop a new source for the production of ethylene and one of the promising ways in this regard is to utilize microorganisms capable of producing ethylene in high productivity.

It is of course known that certain microorganisms can produce ethylene although utilization of a microbiological process for the production of ethylene has been far from practicability due to the scantiness of the amount of ethylene produced. It has been reported that ethylene is produced by Pseudomonas solanacearum as a species of pathogenic bacteria of plants. Further, Goto, et al. have reported recently in Plant Cell Physiology, volume 26, No. 1, pages 141 to 150 (1985) that ethylene can be produced in considerably high productivity by a species of microorganism Pseudomonas syringae pv. phaseolicola which is isolated from morbid punctation of kudzu vine. The productivity of ethylene, however, is still too low by this pseudomonad microorganism to be utilized industrially.

SUMMARY OF THE INVENTION

Therefore, an object of the present invention is to provide a novel microbiological method for industrially producing ethylene and the inventors have undertaken extensive searching works to discover promising microorganisms for ethylene production covering a large number of species of microorganisms including the pathogenic bacteria parasitic on and isolated in a conventional manner from soybean plant in the districts of Akita, Iwate and Ibaraki Prefectures, Japan, and tested the activity of each microorganism for the production of ethylene.

Thus, the method of the present invention for producing ethylene established as a result of the above mentioned investigations comprises culturing a microorganism Pseudomonas syringae pv. glycinea in a culture medium under such conditions that the microorganism produces ethylene and collecting ethylene from the atmospheric gas over the culture medium.

It has also been established that the strains of KN 38, KN 41 and KN 50 are particularly efficient among the microorganisms belonging to P. syringae pv. glycinea for the production of ethylene.

BRIEF DESCRIPTION OF THE DRAWING

The FIGURE is a gas chromatogram of a gaseous mixture as the product of metabolism by P. syringae pv. glycinea KN 38.

DETAILED DESCRIPTION OF THE PREFERRED EMBODIMENTS

As is described in the above given summary, the method of the present invention characteristically utilizes a microorganism named as *P. syringae* pv. *glycinea* isolated from morbid punctation of soybean caused by parasitic bacteria. Among the strains belonging to this bacterial species, the most efficient ones for the production of ethylene include strains KN 38, KN 41 and KN 50 characterized by the following bacteriological properties: Gram-negative; aerobic; short rod-like form; producing green fluorescent coloring matter; no arginine-dihydrolase activity and oxidase activity; unable to grow at 35° C.; no reducing ability for nitrates and unable to anaerobically grow in the presence of nitrates; active for producing levan and inducing hypersensitive reaction of tobacco; negative in rotting of potato tubers, oxidation of gluconic acid, liquefaction of gelatin, hydrolysis of esculin and arbutin and tyrosinase activity; and assimilation of glucose, sucrose and inositol as a single carbon source to proliferate but unable to assimilate trehalose, sorbitol, erythritol, tartaric acid and lactic acid. The bacterial species has pathogenicity against soybean (*Glycine max*) and, by spray innoculation, forms on the soybean leaves water-soaked morbid punctations each of a size of about 3 mm by 5 mm having a color of light brown in the early stage but blackish brown in the late stage.

The above described results support the conclusion that, according to the taxonomical criteria given in Bergey's Manual of Systematic Bacteriology (1984), this bacterial species is *P. syringae* pv. *glycinea*. Accordingly, the inventors have given these bacterial strains the names of *P. syringae* pv. *glycinea* KN 38, KN 41 and KN 50, respectively. These strains were deposited in Institute for Fermentation, Osaka (IFO) under the accession number IFO 14517, IFO 14518 and IFO 14519 respectively, although their deposit in Fermentation Research Institute was unrealizable. The bacterial species utilizable in the method of the present invention is not limited to these strains but may be any of variations belonging to the same species provided that the bacteria can produce ethylene microbiologically. Table 1 below shows the assimilability, i.e. utilizability as a single carbon source, of various organic compounds by the above mentioned particular three strains.

TABLE 1

| Carbon source | KN-38 | KN-41 | KN-50 | Carbon source | KN-38 | KN-41 | KN-50 |
|---|---|---|---|---|---|---|---|
| L-Arabinose | + | + | + | Rhamnose | – | – | – |
| Xylose | + | + | + | Maltose | – | – | – |
| Glucose | + | + | + | Lactose | – | – | – |
| Fructose | + | + | + | Cellobiose | – | – | – |
| Mannose | + | + | + | Trehalose | – | – | – |
| Galactose | + | + | + | Dextrin | – | – | – |
| Sucrose | + | + | + | Starch | – | – | – |
| Raffinose | + | + | + | Inulin | – | – | – |
| Glycerin | + | + | + | Sorbitol | – | – | – |
| Inositol | + | + | + | Erythritol | – | – | – |
| Trigonelline | + | + | + | Galactitol | – | – | – |
| L-Arginine | + | + | + | Salycin | – | – | – |
| Malonic acid | + | + | + | Lactic acid | – | – | – |
| Citric acid | + | + | + | β-Alanin | – | – | – |
| | | | | L-Valine | – | – | – |
| Mannitol | + | + | – | L-Tartaric acid | – | – | – |

In the next place, the culturing conditions are described for the microbiological production of ethylene by use of the above described microorganism. The carbon source to be added to the culturing medium may by any of the organic compounds listed in Table 1 above as assimilable by the microorganism. Particularly preferable among them are sucrose, inositol, trigonelline, raffinose and the like. The amino acids having effectivity in the culture medium for the production of ethylene include asparagine, glutamine, arginine, tryptophan, proline, alanine and the like while methionine known as a precursor of ethylene cannot be assimilated by the microorganisms. Accordingly, the ingredients of the culture medium should preferably include peptone which contains the above named assimilable amino acids. Such a requirement can be met by several known culture media such as the King's B culture medium and YP culture medium in which 5 g of yeast extract and 10 g of peptone are contained per liter of distilled water.

Figure 1:
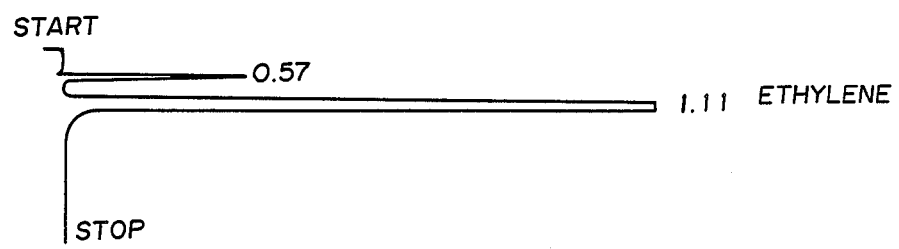

The conditions of culturing should be adequately selected to facilitate proliferation of the above described microorganism efficiently producing ethylene. For example, the value of pH of the culture medium is adjusted in the range from 5 to 8, preferably from 6.5 to 7.5 and the culturing should be continued at a temperature in the range from 20° to 32° C., preferably from 25° to 30° C. until a predetermined amount of ethylene is produced. Generally, culturing is performed for from 1 hour to 5 days, preferably from 1 to 2 days. Although slant culture may be applicable in this case, the culturing should preferably be performed by shaking a liquid culture medium. Other conditions of culturing can readily be determined with reference to the conditions applied to the culturing processes of conventional bacteria. The amount of produced ethylene can be determined by a suitable method such as gas chromatography.

When culturing of the above disclosed microorganism is performed according to the present invention, ethylene is produced microbiologically with a very high efficiency to provide a possibility of at least partly replacing the conventional sources of ethylene utilized in the fields of petrochemical industry and others.

In the following, the method of the present invention is described in more detail by way of examples.

EXAMPLE 1

A King's B culture medium was prepared by dissolving 20 g of peptone, 1.5 g of dipotassium hydrogenphosphate, 1.5 g of magnesium sulfate, 10 ml of glycerin and 15 g of agar in 1000 ml of distilled water. Each of the bacterial strains P. syringae pv. glycinea KN 38 (IFO 14517), KN 41 (IFO 14518) and KN 50 (IFO 14519) was inoculated to 10 ml of the culture medium contained in a test tube of about 30 ml capacity held a slant. The test tubes were each sealed tightly with a rubber stopper and kept standing at 28° C. After 2 days of culturing in this manner, the gas in the test tube was taken and analyzed by gas chromatography for the concentration of ethylene to give the results shown in Table 2 below. The FIGURE in the accompanying drawing is a gas chromatogram obtained with the strain of KN 38, from which it is concluded that the amounts of other by-product gases are very small not to exceed 0.2% so that the desired product of ethylene could be obtained in a high purity. Similar results are obtained with the strains of KN 41 and KN 50.

COMPARATIVE EXAMPLE

For comparison, further culturing tests were performed in substantially the same manner as in Example 1 using known ethylene-producing bacterial species including P. syringae pv. phaseolicola and P. solanacearum to give the results shown in Table 2.

TABLE 2

| Species | Strain | Concentration of ethylene (ppm) |
|---|---|---|
| P. syringae pv. glycinea | KN 38 (IFO 14517) | 447 |
|  | KN 41 (IFO 14518) | 457 |
|  | KN 50 (IFO 14519) | 428 |
| P. syringae pv. phaseolicola | KN 79 | 327 |
|  | KN 81 | 277 |
| P. solanacerum | NIAES 1522 | 0.6 |
|  | NIAES 1520 | 1.72 |

As is clear from the results shown in Table 2, the bacterial species used in the inventive method can produce ethylene with outstandingly high productivity in comparison with known ethylene-producing bacterial species.

EXAMPLE 2

Each of the bacterial species P. syringae pv. glycinea KN 38 (IFO 14517), KN 41 (IFO 14518) and KN 50 (IFO 14519) was inoculated to a 20 ml portion of a King's B culture medium prepared in the same formulation as in Example 1, YP culture medium prepared in the formulation described before or bouillon culture medium prepared by dissolving 10 g of meat extract, 10 g of peptone and 1 g of sodium chloride in 1000 ml of distilled water as contained in an Erlenmeyer flask of about 100 ml capacity. The flask was sealed with a rubber stopper and culturing of the bacteria was performed by shaking the flask at 28° C. After 24 hours of culturing in this manner, the gas in the flask was taken out and analyzed by gas chromatography for the concentration of the microbiologically produced ethylene to give the results shown in Table 3 below.

TABLE 3

| Strain of P. syringae pv. glycinea | Concentration of ethylene (ppm) | | |
|---|---|---|---|
|  | YP medium | King's B medium | Bouillon medium |
| KN 38 (IFO 14517) | 80.3 | 113.6 | 48.3 |
| KN 41 (IFO 14518) | 102.0 | 209.0 | 74.0 |
| KN 50 (IFO 14519) | 56.2 | 134.9 | 81.1 |

What is claimed is:

1. A method for microbiologically producing ethylene which comprises culturing a bacterial microorganism of Pseudomonas syringae pv. glycinea in a culture medium to form ethylene and collecting said ethylene and wherein the microorganism is selected from the group consisting of the strains of P. syringae pv. glycinea KN 38 (IFO 14517), KN 41 (IFO 14518) and KN 50 (IFO 14519).

2. The method for microbiologically producing ethylene as claimed in claim 1, wherein the culturing is carried out at a pH of from 5 to 8 and a temperature of from 20° to 32° C.

3. The method for microbiologically producing ethylene as claimed in claim 1, wherein the culturing is carried out at a pH of from 6.5 to 7.5 and a temperature of from 25° to 30° C.

4. The method of claim 2, wherein the microorganism is cultured for from 1 hour to 5 days.

5. The method of claim 2, wherein the microorganism is cultured for 1 to 2 days.

6. The method of claim 3, wherein the microorganism is cultured for from 1 hour to 5 days.

7. The method of claim 3, wherein the microorganism is cultured for 1 to 2 days.

* * * * *